United States Patent
Phillips et al.

(10) Patent No.: US 11,223,227 B1
(45) Date of Patent: Jan. 11, 2022

(54) MEDICAL CART PROVIDING DATA CONTINUITY

(71) Applicant: Capsa Solutions LLC, Portland, OR (US)

(72) Inventors: Justin Phillips, Troutdale, OR (US); John St. Pierre, Portland, OR (US); Rody Hardy, Portland, OR (US)

(73) Assignee: Capsa Solutions LLC, Portland, OR (US)

(*) Notice: Subject to any disclaimer, the term of this patent is extended or adjusted under 35 U.S.C. 154(b) by 0 days.

(21) Appl. No.: 16/919,557

(22) Filed: Jul. 2, 2020

Related U.S. Application Data

(60) Provisional application No. 62/870,088, filed on Jul. 3, 2019.

(51) Int. Cl.
| | |
|---|---|
| *H02J 9/06* | (2006.01) |
| *G06F 1/26* | (2006.01) |
| *H02J 7/02* | (2016.01) |
| *B60R 16/033* | (2006.01) |
| *A61B 50/13* | (2016.01) |
| *H02J 7/00* | (2006.01) |
| *G16H 40/67* | (2018.01) |

(52) U.S. Cl.
CPC ............... *H02J 9/06* (2013.01); *A61B 50/13* (2016.02); *B60R 16/033* (2013.01); *G06F 1/263* (2013.01); *H02J 7/0048* (2020.01); *H02J 7/02* (2013.01); *G16H 40/67* (2018.01)

(58) Field of Classification Search
CPC ... H02J 9/06; H02J 7/0048; H02J 7/02; A61B 50/13; B60R 16/033; G06F 1/263; G16H 40/67
See application file for complete search history.

(56) References Cited

U.S. PATENT DOCUMENTS

| | | | |
|---|---|---|---|
| 4,860,185 A | 8/1989 | Brewer et al. | |
| 5,825,100 A * | 10/1998 | Kim | H02J 9/06 307/66 |
| 6,445,089 B1 | 9/2002 | Okui | |
| 6,735,096 B2 | 5/2004 | Chang et al. | |
| 6,766,218 B2 | 7/2004 | Rosenblum | |
| 7,014,486 B1 * | 3/2006 | Wu | G06F 1/1632 439/165 |
| 7,160,113 B2 | 1/2007 | McConnell et al. | |
| 7,164,214 B2 | 1/2007 | Eisenberger et al. | |
| 7,183,748 B1 | 2/2007 | Unno et al. | |
| 7,259,477 B2 | 8/2007 | Klikic et al. | |
| 7,518,265 B2 | 4/2009 | Roepke | |
| 7,737,581 B2 | 6/2010 | Sprulin et al. | |
| 7,782,607 B2 | 8/2010 | Harbin et al. | |
| 7,800,255 B2 | 9/2010 | Coonan et al. | |
| 7,830,668 B2 | 11/2010 | Coonan et al. | |
| 7,843,676 B2 | 11/2010 | Klikic et al. | |
| 7,855,530 B2 | 12/2010 | Coonan et al. | |
| 8,076,799 B2 | 12/2011 | Wu et al. | |

(Continued)

*Primary Examiner* — Daniel Kessie
(74) *Attorney, Agent, or Firm* — Standley Law Group LLP; Adam J. Smith; Jeffrey S. Standley

(57) ABSTRACT

A medical cart providing data continuity, and methods regarding the same, are provided. A holder associated with a body of the cart is configured to receive a removeable battery having a terminal. A connector located at the holder is positioned to receive the terminal when the removeable battery is received within the holder. A power bus is in electrical connection with the connector and an alternative power source. A controller in electrical connection with the power bus automatically begins utilizing the alternative power source following a determination that a loss of power event has occurred.

14 Claims, 14 Drawing Sheets

(56) References Cited

U.S. PATENT DOCUMENTS

| | | | |
|---|---|---|---|
| 8,138,910 B2 | 3/2012 | Iwai | |
| 8,160,727 B2 | 4/2012 | Coonan et al. | |
| 8,227,943 B2 | 7/2012 | Harbin et al. | |
| 8,398,408 B1 * | 3/2013 | Hansen | A61B 8/4433 439/34 |
| 8,413,947 B2 * | 4/2013 | Chiang | B62M 6/90 248/553 |
| 8,775,828 B2 | 7/2014 | Coonan et al. | |
| 9,801,791 B2 | 10/2017 | Reckelhoff et al. | |
| 9,914,501 B2 * | 3/2018 | Marioni | B60L 3/12 |
| 10,029,754 B2 * | 7/2018 | Watarai | B62M 25/08 |
| 10,965,052 B2 * | 3/2021 | Shikanai | H01R 13/17 |
| 2004/0026587 A1 * | 2/2004 | Cox | H01M 50/20 248/316.7 |
| 2004/0203267 A1 * | 10/2004 | Chen | F16M 13/00 439/76.1 |
| 2006/0097886 A1 * | 5/2006 | Jones | G06F 1/30 340/680 |
| 2007/0037045 A1 * | 2/2007 | Takeshita | H01M 50/147 429/96 |
| 2009/0212738 A1 * | 8/2009 | Coonan | H02J 7/0045 320/113 |
| 2012/0322321 A1 * | 12/2012 | Kwag | H01R 33/765 439/754 |
| 2013/0326237 A1 * | 12/2013 | Holdengreber | H02J 9/061 713/300 |
| 2014/0152099 A1 * | 6/2014 | Boyd | H02J 9/061 307/23 |
| 2015/0210351 A1 * | 7/2015 | Tagaya | B62M 6/90 280/288.4 |
| 2016/0126513 A1 * | 5/2016 | Mifsud | H01M 10/623 429/82 |
| 2016/0268822 A1 * | 9/2016 | Toya | H02J 7/0047 |
| 2017/0141597 A1 * | 5/2017 | Mifsud | H02J 7/00036 |
| 2020/0206400 A1 * | 7/2020 | Shinohara | A61M 60/871 |
| 2020/0295327 A1 * | 9/2020 | Onishi | B60L 50/66 |
| 2020/0330263 A1 * | 10/2020 | Dabrowiak | H02J 7/0013 |

* cited by examiner

MEDICAL CART PROVIDING DATA CONTINUITY

CROSS-REFERENCE TO RELATED APPLICATIONS

This application claims the benefit of U.S. Provisional Patent Application No. 62/870,088 filed Jul. 3, 2019, the disclosures of which are hereby incorporated by reference as if fully restated herein.

TECHNICAL FIELD

Exemplary embodiments relate generally to medical carts with data continuity.

BACKGROUND AND SUMMARY OF THE INVENTION

Carts are often used in medical facilities for a variety of tasks. Such carts may be used, for example without limitation, to store and dispense medications, to input, store, and display electronic medical record information, to provide work stations and platforms, to store medical equipment, and the like. Such carts generally have a number of systems and components which require electrical power. Electrical power is often provided by way of one or more batteries. Sometimes, a cart has a first, external battery which is capable of being removed for charging, replacement, maintenance, and the like. In such cases, the cart may have a second, internal battery and/or connection to an external power source (e.g., plug) to facilitate the ongoing supply of electrical power. In some cases it may be desirable to know in advance of the removal of the first battery to prevent power interruption, voltage spikes, or high in-rush current situations, all of which may result in damage or otherwise undesirable behavior to the end user. Therefore, in some situations it may be desirable to detect imminent battery removal.

Certain systems and methods for detecting imminent battery removal are provided. In an exemplary embodiment, a cart may comprise a holder pivotably mounted thereto and configured to receive a battery. The holder may comprise battery terminals which facilitate electrical connection between the battery and a power bus while the battery is installed within the holder. The holder may rotate between a secured position and an unsecured position. While not in the unsecured position, the battery may be physically blocked from removal by way of an obstruction. A sensor may be positioned to detect movement of the holder from the secured position. The sensor may alert the power bus, which may upon such movement, disconnect from the battery and begin drawing upon a second battery or another power source as needed. However, the battery may remain electrically connected to the power bus during some or all of the time that the holder is moved between the secured and unsecured position. In exemplary embodiments, the battery remains electrically connected to the power bus by way of one or more battery terminals installed in the bottom of the holder such that the power bus is capable of drawing upon the battery, even when the holder is located in the unsecured position. The time it takes to move the holder from the secured position to the unsecured position may be long enough for the power bus to switch over to the second battery. In this way, the adverse effects associated with sudden disconnection from a power supply may be avoided.

In other exemplary embodiments, the first battery may be configured to fit within a holder. The holder may comprise an obstruction which permits the removal of the first battery unless and until the first battery is rotated away from the holder. A switch may be provided within the holder for detecting the presence of the first battery. A connector for the battery terminals of the first battery may pivot to maintain an electrical connection with the first battery while the first battery is rotated. A protrusion within the holder may fit within a cavity of the first battery, but be configured to permit the aforementioned rotation. The cart may switch to the second battery when the first battery is moved and the switch deactivated.

In some cases, there is no way to know that the first battery will be removed. For example, the cart may collide with a wall, personnel, another cart, or the like and the first battery may become dislodged. Still other problems, such as malfunctions, may result in power interruption where no advance notice can be given. Therefore, in some situations it may be desirable to switch power supplies automatically.

A cart configured to source power from a back-up power supply automatically upon determination of an unanticipated loss of power event from the first battery is provided, along with methods for operating the same. The cart may comprise a holder configured to receive a first, removeable battery. The holder may comprise battery terminals which facilitate electrical connection between the first battery and a power bus while the first battery is installed within the holder. The cart may comprise a second, back-up battery. A power bus may be electrically connected to the first, removeable battery and the second, back-up battery. The unanticipated loss of power event may be determined by certain electrical changes occurring after the first battery is unexpectedly removed, such as but not limited to, voltage spikes, voltage drops, current spike, current drops, capacity drops, some combination thereof, or the like. The unanticipated loss of power may be indicated to the user such that the user may go about restoring the first battery power, such as by replacing the first battery with another battery, recharging the first battery, supplying alternative power (e.g., plugging the cart into a wall outlet), or the like. Power sourcing may be of just the first battery or just the second battery, or some combination thereof. Such automatic changing of supplied power may be accomplished without the need for any detection of user interaction, especially preemptive indication of user interaction.

In some cases, users choose to remove the first battery from the cart before it is completely discharged. For example, the user might remove the first battery at the end of their shift for recharging, even though the battery is still at 50 percent capacity. Similarly, the cart may periodically run on a second battery for a period of time while a first battery is swapped without completely discharging. This may result in battery memory effects, which may result in the battery having reduced capacity and other issues over time. Such memory affects may apply to one or both of the first battery and the second battery. Therefore, in some situations it may be desirable to change the power supply automatically after complete, or near complete, discharge of the first and/or second battery.

A medical cart which changes power supply automatically upon complete, or near complete, discharge is provided. A cart may comprise a holder configured to receive a first, removeable battery. The holder may comprise battery terminals which facilitate electrical connection between the first battery and a power bus while the first battery is installed within the holder. The cart may comprise a second, back-up battery. A power bus may be electrically connected to the first, removeable battery and the second, back-up battery. The cart may be configured to draw upon the first battery until the first battery is exhausted. Once exhausted, the cart may be configured to automatically source power from the second, back-up battery. Once the back-up battery is exhausted, the cart may be configured to automatically source power again from the first battery. In this way, the cart may be configured to continuously move between fully exhausting the first battery and fully exhausting the second battery to preserve continuity of data in a way which also reduces or eliminates battery memory effects. Indication may be provided at the cart that the external battery is exhausted such that the external battery may be recharged or swapped with another battery or an alternative power source (e.g., outlet power) may be utilized. Power sourcing may be of just the first battery or just the second battery, or some combination thereof. Such automatic changing of supplied power may be accomplished without the need for any detection of user interaction, especially preemptive indication of user interaction.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1A:
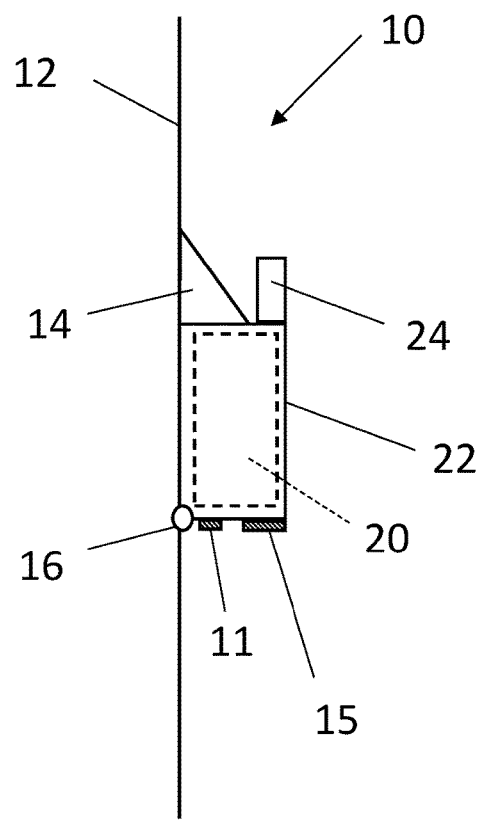
FIG. 1A is a side view of an exemplary holder with an exemplary battery in a secured position.
Figure 1B:
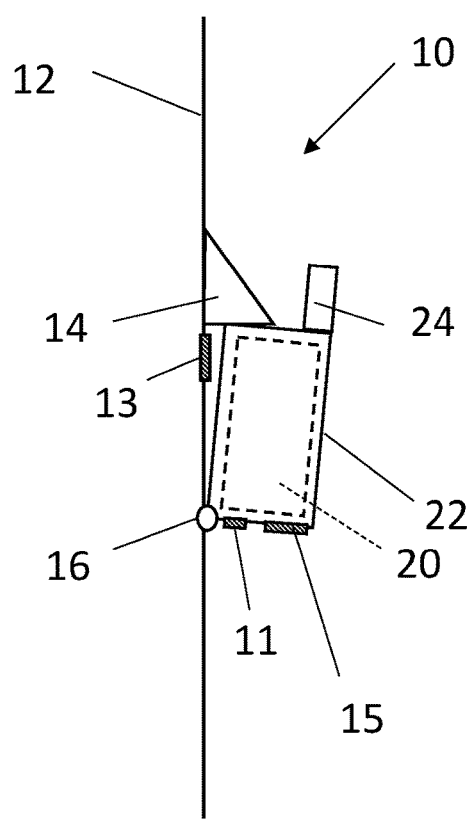
FIG. 1B is a side view of the holder of FIG. 1A in a partially unsecured position.
Figure 1C:
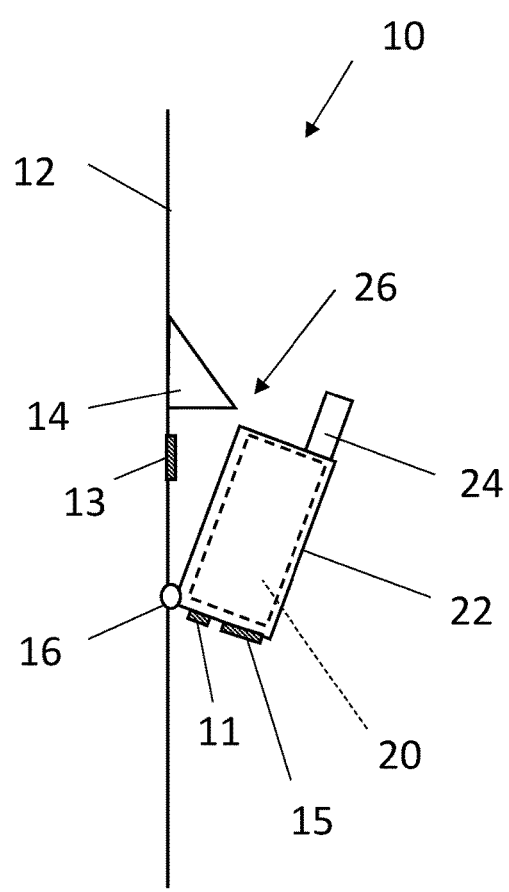
FIG. 1C is a side view of the holder of FIG. 1A in a fully unsecured position.
Figure 1D:
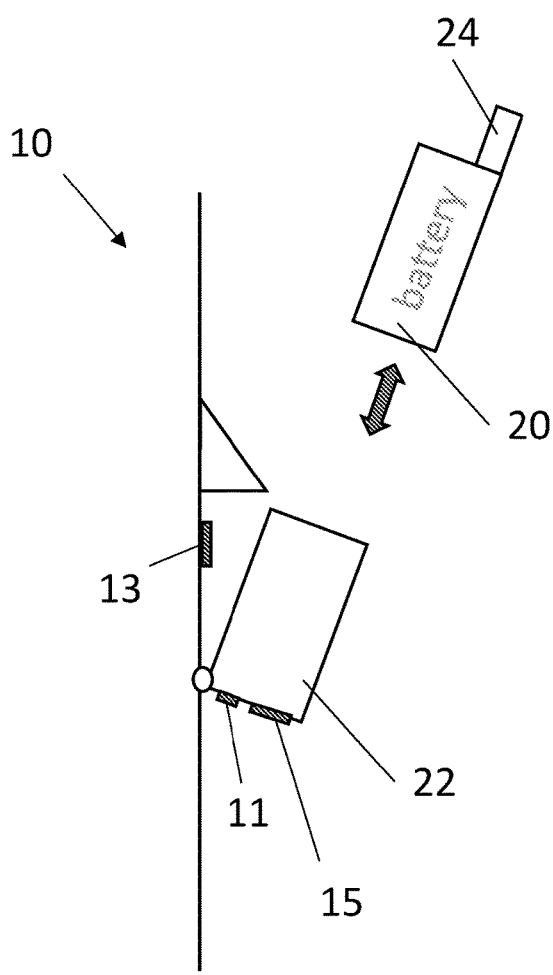
FIG. 1D is a side view of the battery of FIG. 1A removed from the holder.

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

FIGS. 1A-1D are simplified diagrams of a portion of a medical cart 10 comprising a holder 22 configured for movement between a secured position (FIG. 1A), a partially unsecured position (FIG. 1B), and an unsecured position (FIG. 1C-1D) which permits removal or insertion of a battery 20. A pivot device 16 may be installed to a surface 12 of the medical cart 10. The pivot device 16 may be connected to the holder 22. The holder 22 may define a container or receptacle sized to accommodate the battery 20. The holder 22 may be configured to accommodate one of a number of interchangeable batteries 20 in exemplary embodiments. The pivot device 16 may comprise a hinge, bearing, or other rotational mechanism which permits the holder 22 to be rotated towards and away from the surface 12 of the cart 10.

The pivot device 16 may be configured to permit the holder 22, and thus the battery 20 when installed, to be moved between a secured position, whereby the holder 22 extends parallel to, and/or rests against, the surface 12, and an unsecured position whereby the holder 22 is positioned at an angle from the surface 12. The pivot device 16 may have a limited range of motion which limits the distance the holder 22 may be rotated away from the surface 12 so as to prevent the battery 20 from falling out when the holder 22 is in the unsecured position. Alternatively, or additionally, the holder 22 may comprise one or more mechanisms configured to temporarily secure the battery 20 such as, but not limited to, magnets, press fits, mating protrusions and recesses, notches, locks, some combination thereof, or the like.

An obstruction 14 may protrude from the surface 12. The obstruction 14 may be configured to prevent the battery 20 from being removed from, or inserted into, the holder 22 when the holder 22 is in the secured position and/or the partially unsecured position. The obstruction 14 may be configured to allow the battery 20 to be removed from, or inserted into, the holder 22 when the holder 22 is in the fully unsecured position. While in the fully unsecured position, a gap 26 may be formed between the obstruction 14 and the holder 22 such that the battery 20 may be removed from, or inserted into, the holder 22. The battery 20 may comprise a handle 24 which may facilitate removal and insertion of the battery 20 into or from the holder 22. Alternatively, or additionally, the same or a different handle 24 may be located on the holder 22 to facilitate rotational movement of the holder 22. While the obstruction 14 is illustrated as triangular in shape, those of skill in the art will recognize that any size or shape obstruction 14 is contemplated. A combination of obstructions 14 may be utilized in certain embodiments.

The holder 22 may comprise a first sensor 11. The first sensor 11 may be configured to detect whether the battery 20 is installed within the holder 22. The first sensor 11 may comprise a pressure sensor, weight sensor, proximity sensor, light sensor, switch, some combination thereof, or the like. In exemplary embodiments, the first sensor 11 may be located along a bottom surface of the holder 22 such that the battery 20 contacts the first sensor 11 upon insertion within the holder 22, though such is not required.

A second sensor 13 may be located at the surface 12. The second sensor 13 may be configured to detect whether the holder 22 is in the secured and/or unsecured position. The second sensor 13 may comprise a pressure sensor, weight sensor, proximity sensor, light sensor, switch, some combination thereof, or the like. In exemplary embodiments, the second sensor 13 may be located below the obstruction 14 such that the holder 22 contacts the second sensor 13 upon placement in the secured position against or parallel to the surface 12, though such is not required.

Alternatively, or additionally, the second sensor 13 may comprise a movement-based sensor such as, but not limited to, an accelerometer, angle sensor, some combination thereof, or the like. In such embodiments, the second sensor 13 may be configured to detect movement of the holder 22 and/or the rotational device 16.

To remove or insert the battery 20, a user may pivot the holder 22 away from the surface 12 by pulling on the handle 24 to create the gap 26 such that the battery 20 may clear the obstruction 14. The pivot device 16, the holder 22, the surface 12, and/or the obstruction 14 may be configured to require a predetermined amount or force to initially move the holder 22 from the secured position. Once rotated to the unsecured position, the battery 20 may be removed by pulling the handle 24 and lifting the battery 20 out of the holder 22. Once rotated to the unsecured position, the battery 20 may be inserted by grasping the handle 24 and placing the battery 20 within the holder 22. The obstruction 14 may be sized, shaped, or otherwise configured to prevent removal or insertion of the battery 20 while the holder 22 is in the secured position and the partially unsecured position and permit removal or insertion of the battery 20 while the holder 22 is in the unsecured position.

The holder 22 may further comprise one or more battery terminals 15. The battery terminals 15 may comprise any device which facilitates electrical connection with the battery 20. In exemplary embodiments, the battery terminals 15 may be located along a bottom surface of the holder 22, though such is not required.

Figure 2A:
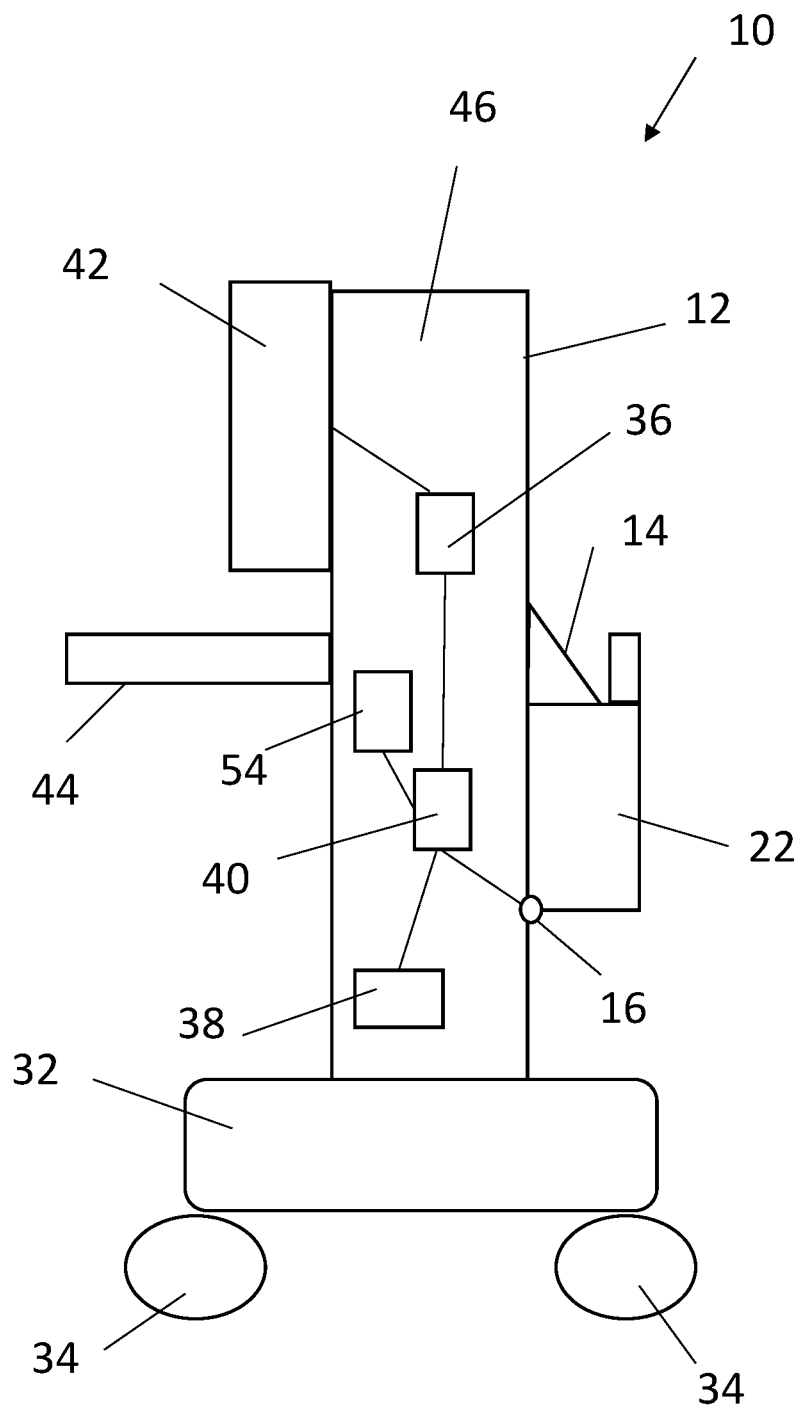
FIG. 2A is a side view of an exemplary cart with the holder of FIG. 1A in the secured position.
Figure 2B:
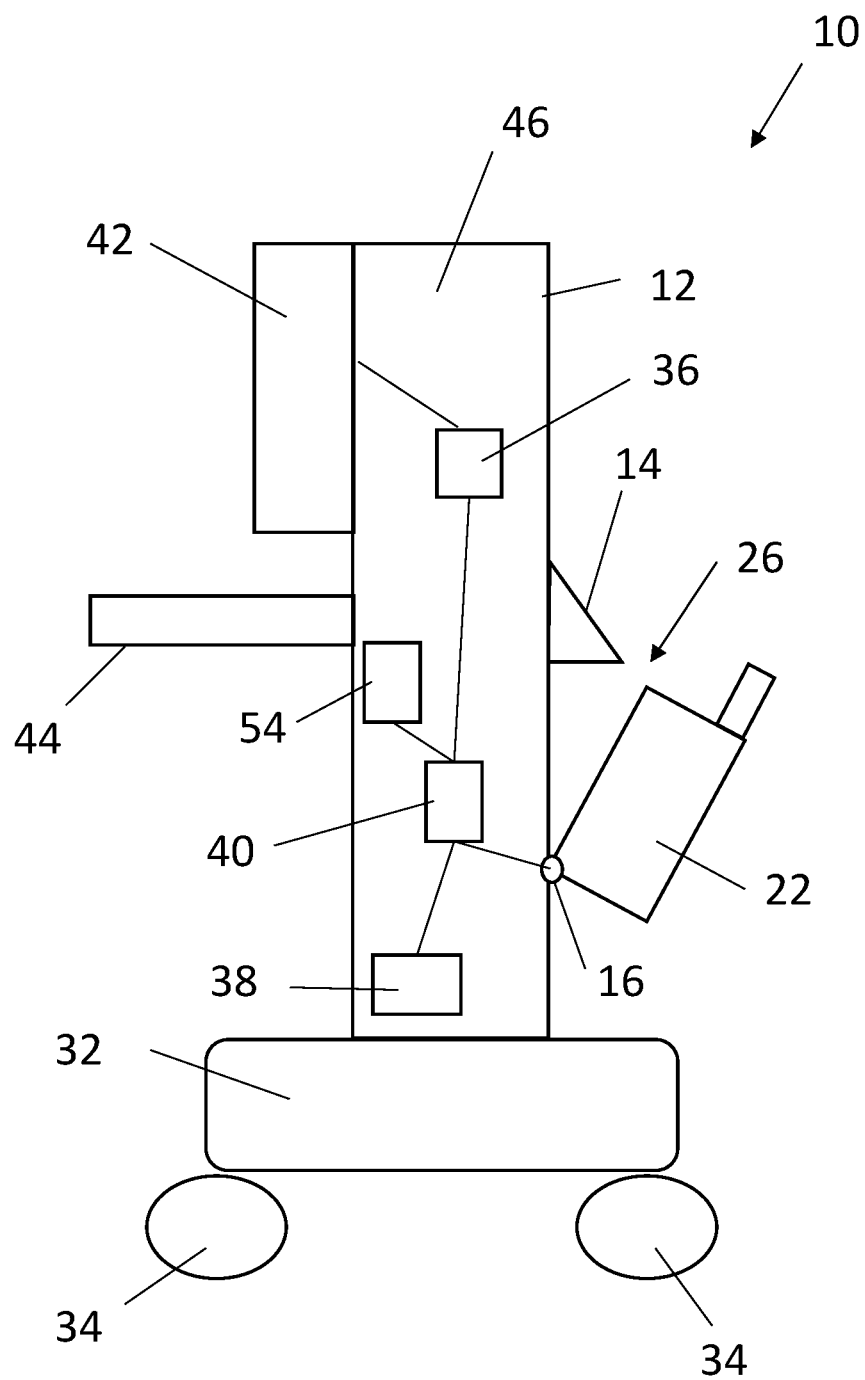
FIG. 2B is a side view of the cart of FIG. 2A with the holder in the unsecured position.

FIGS. 2A-2B illustrate an exemplary cart 10 with the holder 22 in the secured position (FIG. 2A) and the fully unsecured position (FIG. 2B). The cart 10 may be any kind of cart 10 comprising any number of features and/or components. The cart 10 may comprise a body 46, a base 32, wheels 34, and a work platform 44, to name a few examples. The cart 10 may further comprise one or more displays 42. In particular, the cart 10 may be a medical cart for use in hospitals, doctor's offices, skilled care facilities, nursing homes, and other medical care facilities. The cart 10 may be configured, for example without limitation, to store and dispense medications, to input, store, and display electronic medical record information, to provide work stations and platforms, to store medical equipment, some combination thereof, and the like. The illustrated cart 10 is shown merely for exemplary purposes and is not intended to be limiting. For example, without limitation, the body 46, base 32, wheels 32, and work platform 44 may be provided in any size and/or shape, in addition to other components, and/or may be excluded.

The cart 10 may comprise a number of electrical components 36 placed in electrical connection with the battery 20. In exemplary embodiments, such electrical connection may be made by way of a power bus 40 and/or one or more battery terminals 15. The electrical connection may be maintained while the holder 22 is rotated between the secured, the partially unsecured, and the fully unsecured positions. The electrical connection to the battery 20 may be lost only upon removal of the battery 20 from the holder 22. In exemplary embodiments, the battery 20 is capable of remaining electrically connected to the power bus 40 by way of one or more battery terminals 15 such that the power bus 40 is capable of drawing upon the battery 20, even when the holder 22 is located in the fully unsecured position.

The electrical components 36 may also be electrically connected to a second battery 38. Both the first battery 20 and the second battery 38 may be configured to operate the cart 10 and various functions and components thereof for the same or different periods of time. The battery 20 may be external, while the second battery 38 may be internal, though such is not required. In other exemplary embodiments, an external power source may be used in lieu of, or in addition to, the second battery 38, such as but not limited to, a plug for connecting to a wall outlet. The electrical components 36 may be electrically connected to the battery 20 and the second battery 38 by way of the power bus 40. One such electricity consuming component 36 may be the one or more displays 42, which may comprise an electronic display. Other such electricity consuming components 36 include, for example without limitation, computers, displays, touch screens, user interfaces, medical equipment, locking devices, motors, lift mechanisms, locking bins, lights, some combination thereof, or the like.

In exemplary embodiments, the power bus 40 may be in electrical connection with a controller 54. The controller 54 may be configured to control certain operations of the cart 10 shown and described herein.

Figure 3:
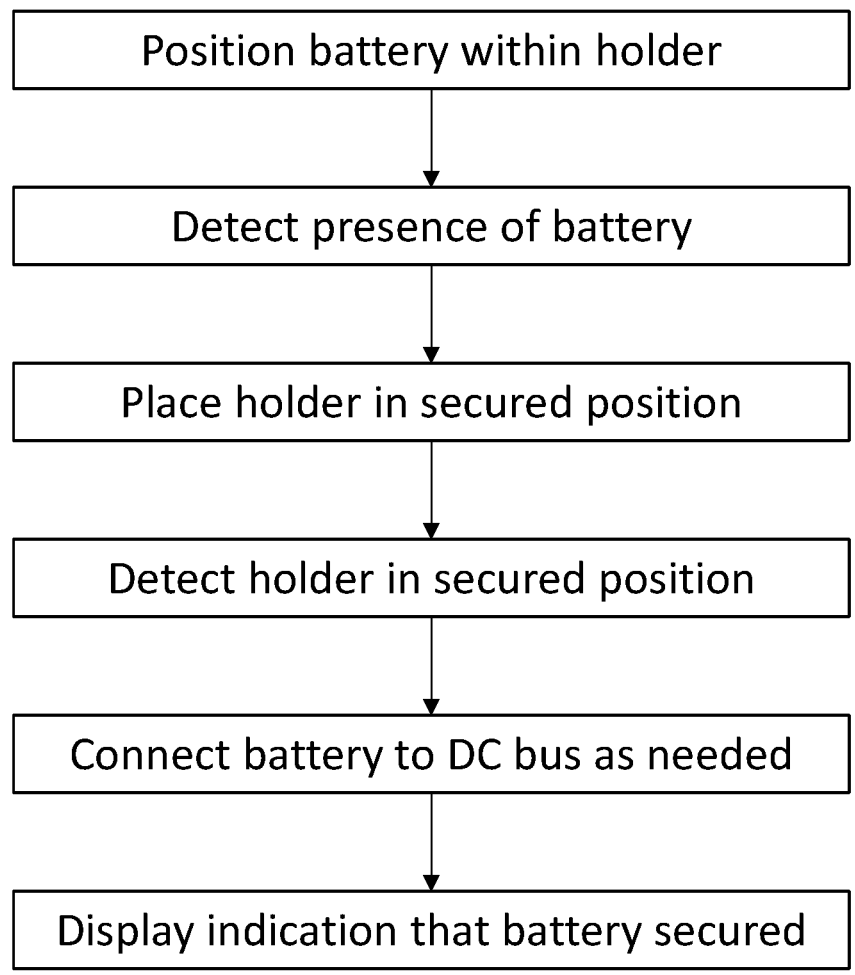
FIG. 3 is a flow chart with exemplary logic for use with the cart of FIGS. 1A-2B.

FIG. 3 is a flow chart with exemplary logic for installing the removable battery 20. The removable battery 20 may be secured within the holder 22. The presence of the battery 20 may be detected by the first sensor 11. In exemplary embodiments, the presence of the battery 20 may be indicated to the user, such as by display at the display 42, audible alert, notification, some combination thereof, or the like. The holder 22 may be placed in the secured position. Placement of the holder 22 in the secured position may be detected by the second sensor 13. In exemplary embodiments, placement of the holder 22 in the secured position may be indicated to the user, such as by display at the display 42, audible alert, notification, some combination thereof, or the like. In exemplary embodiments, the cart 10 may be configured to draw upon the removeable battery 20 as needed or programmed when the holder 22 is placed in the secured position. For example, the cart 10 may be configured to prevent drawing power from the battery 20 until the holder 22 is placed in the secured position and thus blocked from removal by the obstruction 14. Operations described herein may be performed, at least in part, by instruction from the controller 54.

Figure 4:
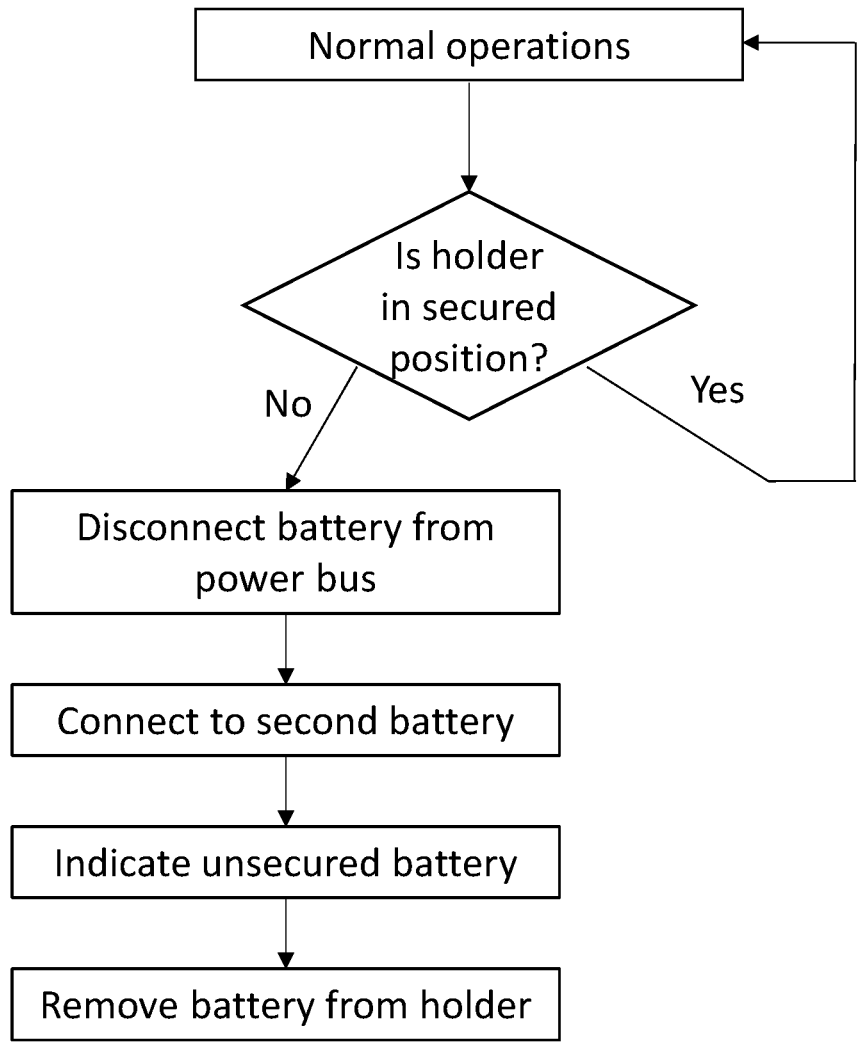
FIG. 4 is a flow chart with exemplary logic for use with the cart of FIGS. 1A-2B.

FIG. 4 is a flow chart with exemplary logic for removing the battery 20. The cart 10 may be configured to periodically or continually monitor for movement of the holder 22. Once it is determined that the holder 22 is out of the secured position, such as in the partially and/or fully unsecured positions, the cart 10 may be configured to stop or continue not drawing power from the first battery 20. The cart 10 may be configured to begin utilizing the second battery 38 and/or an alternative power source as needed or otherwise programmed. Movement of the holder 22 from the secured position may be detected by the second sensor 13. Placement of the holder 22 in the partially or fully unsecured position may be indicated to the user, such as by display at the display 42, audible alert, notification, some combination thereof, or the like. Once in the fully unsecured position, the battery 20 may be removed from the holder 22. The time it takes to move the holder 22 from the secured position to the fully unsecured position may provide sufficient time for the cart 10 to begin sourcing power only from the second battery 38 and/or an alternative power source. Removal of the battery 20 from the holder 22 may be detected by the first sensor 11 and indicated to the user, such as by display at the display 42, audible alert, notification, some combination thereof, or the like.

For clarity, in exemplary embodiments, the potential for an electrical connection between the battery 20 and the power bus 40 may be maintained while the holder 22 is rotated. In this way, the power bus 40 may continue to draw upon the battery 20 while the holder is rotated 22. The potential for an electrical connection may be terminated, in exemplary embodiments, only upon removal of the battery 20 from the holder 22. However, the cart 10 may be configured to cease drawing upon the battery 20 once it is determined, or at some point following, that the holder 22 is no longer in the secured position. In this way, adequate time is allotted for switchover to the second battery 38 and/or alternative power source such that constant electrical supply is maintained and the negative effects of interrupted power are not experienced.

Operations described herein may be performed, at least in part, by instruction from the controller 54.

Figure 5:
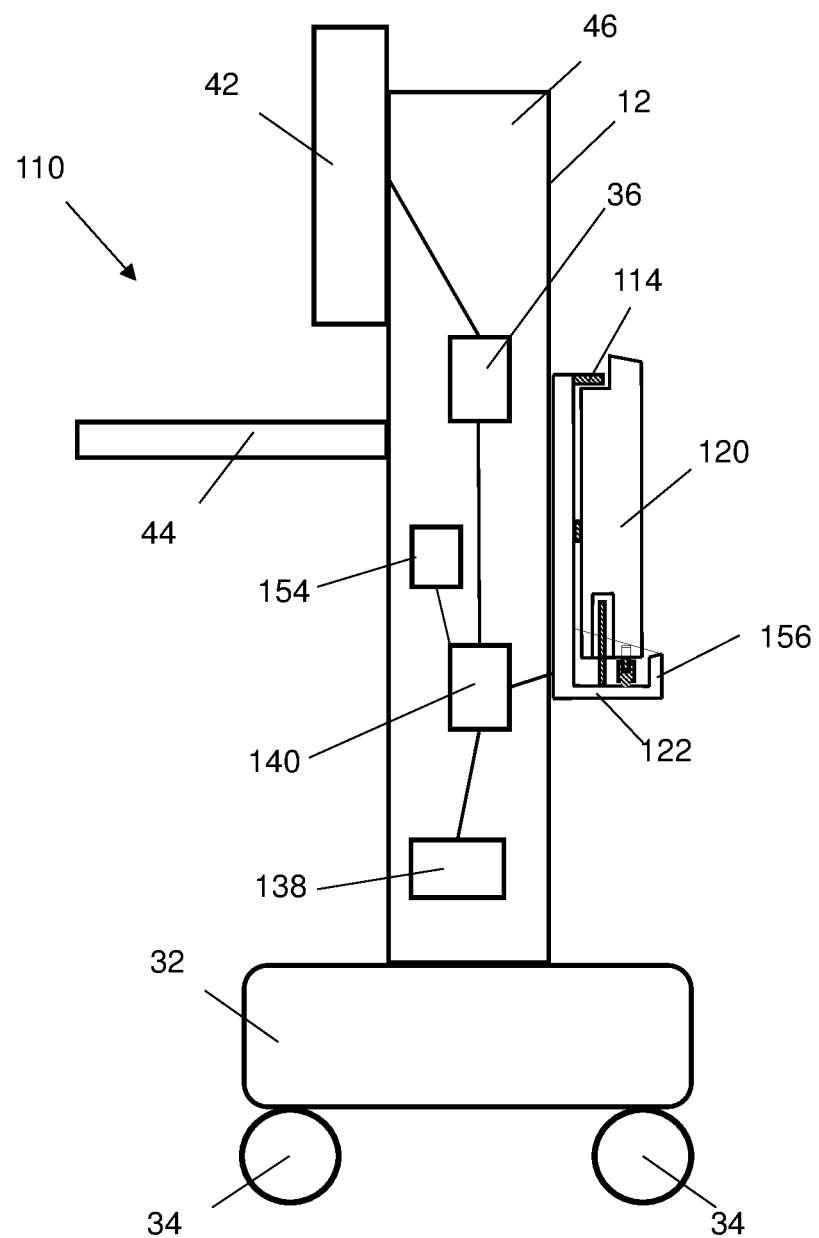
FIG. 5 is a side view of another exemplary embodiment of the cart with another exemplary battery removal detection system.
Figure 6A:
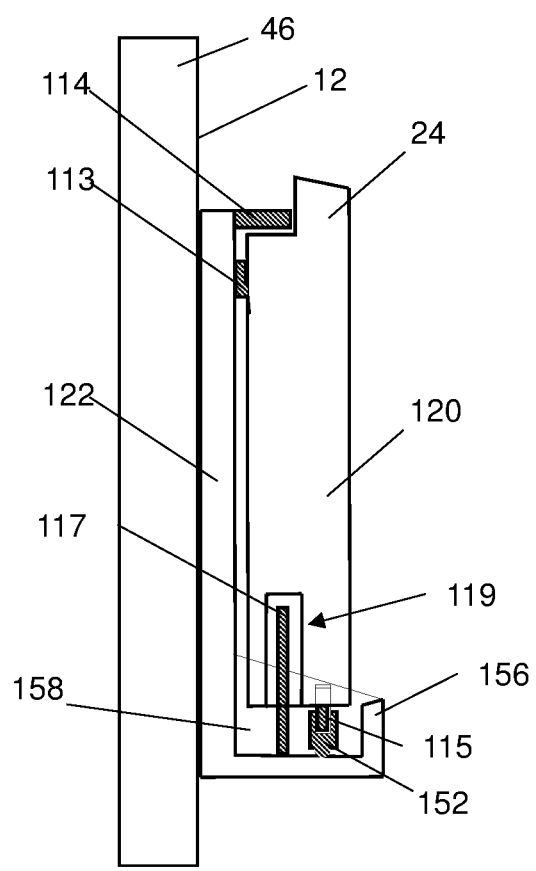
FIG. 6A is a detailed side view of the battery removal detection system of FIG. 5 with the removeable battery in a secured position.
Figure 6B:
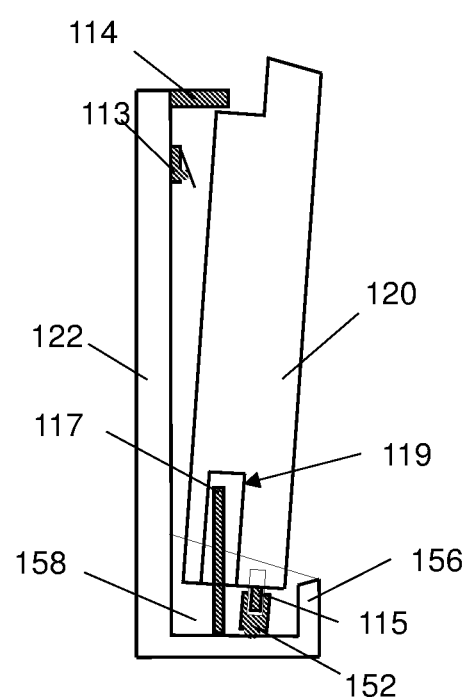
FIG. 6B is a detailed side view of the battery removal detection system of FIG. 5 with the removeable battery in a partially unsecured position.
Figure 6C:
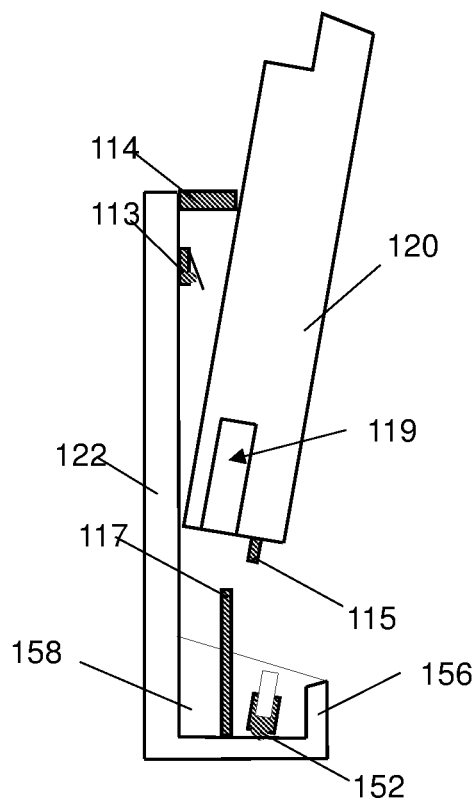
FIG. 6C is a detailed side view of the battery removal detection system of FIG. 5 with the removeable battery in a fully unsecured position.
Figure 6D:
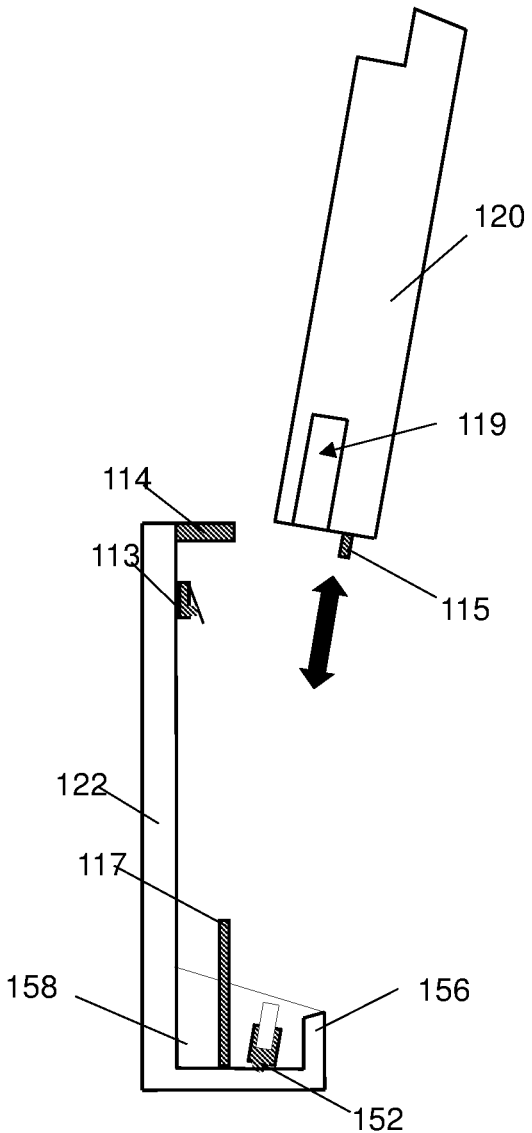
FIG. 6D is a detailed side view of the battery removal detection system of FIG. 5 with the removeable battery removed from the holder.

FIG. 5 illustrates another exemplary cart 110. A holder 122 may be mounted to the cart 110. The holder 122 may be configured to removably accept a first battery 120. The first battery 120 may be configured to power the cart 110 for a period of time. Such period of time may be at least a number of minutes, for example. The holder 122 may be configured to interchangeably receive one of a number of identical or similar such batteries 120. The holder 122 may comprise one or more obstructions 114 configured to prevent removal of a secured one of the removable batteries 120 without movement of the battery 120.

A power bus 140 may be electrically connected to the first battery 120 when installed at the holder 122. The power bus 140 may be electrically connected to a back-up power source 138. The back-up power source 138 may be configured to power the cart 110 for a period of time. Such period of time may be at least a number of minutes, for example. The back-up power source 138 may be permanently, or semi-permanently installed at the cart 110 such that it is not capable of being readily removed, such as without particular tools. The back-up power source 138 may comprise one or more batteries, generators, plug for wall outlet, some combination thereof, or the like.

In exemplary embodiments, the power bus 140 may be in electrical connection with a controller 154. The controller 154 may be configured to control certain operations of the cart 110 shown and described herein.

FIGS. 6A-6D illustrate detailed views of the holder 122, battery 120, and other components. The holder 122 may comprise a protrusion 117. The battery 120 may comprise a cavity 119 configured to receive the protrusion 117. Any shape, size, or type of cavity 119 and/or protrusion 117 may be utilized. Multiple protrusions 117 and cavities 119 may be utilized. In exemplary embodiments, the cavity 119 may be complementary to the protrusion 117, however, sufficient clearance may be provided to permit rotation or other movement of the battery 120 between the secured, partially unsecured, and fully unsecured positions such that the battery 120 may be positioned to clear the obstruction for removal from, or insertion into, the holder 122. The cavity 119 and protrusion 117 may be configured to mate to guide the battery 120 into the holder 122 and maintain its position within the holder 122 until manually removed by the user. The holder 112 may comprise a front lip 156 and/or side walls 158 configured to assist with securing the battery 120 within the holder 122 during such removal and insertion.

A switch 113 may be provided within the holder 112. The switch 113 may be configured to detect the battery 120 when it is secured within the holder 122. For example, without limitation, the switch 113 may be deactivated when the battery 120 is in the partially and/or fully unsecured positions and may be activated when the battery 120 is in the fully secured position. Other sensors may be used in conjunction with, or alternatively to, the switch 113.

A connector 152 may be provided within the holder 122. One or more terminals 115 may be provided at the battery 120. When the battery 120 is in the secured, partially unsecured, and/or fully unsecured positions, the connector 152 may be configured to maintain a potential electrical connection with the terminals 115 on the battery 120. In exemplary embodiments, without limitation, the connector 152 may be provided with a swivel, spring, extension device, some combination thereof, or the like to maintain the potential for such a connection. The cavity 119 and the protrusion 117 may be configured to align the connector 152 with the terminals 115 when the battery 120 is installed and removed from the holder 112. The obstruction 114 may be configured to prevent manual removal of the battery 120, and thus breaking of the connection between the connector 152 and the terminals 115, prior to the battery 120 being placed in the fully unsecured position.

The fully secured position may include placing the battery 120 vertically within the holder 122, though any position may be utilized. The partially and fully unsecured positions may comprise rotating the battery 120 away from the body 46 at an increasing angle.

Figure 7:
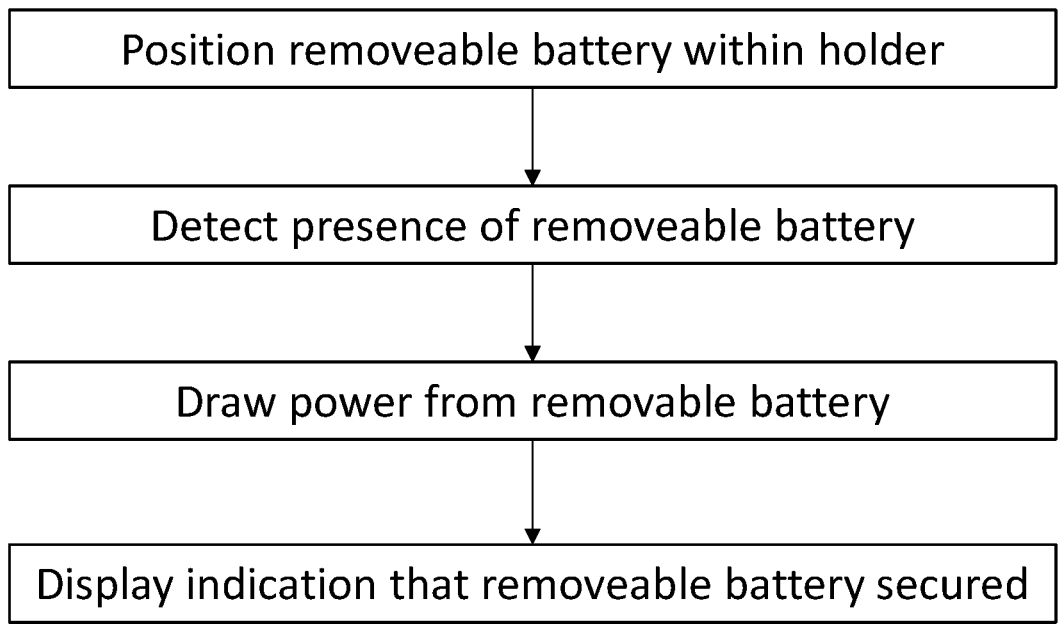
FIG. 7 is a flow chart with exemplary logic for operating the cart of FIGS. 5-6D.
Figure 8:
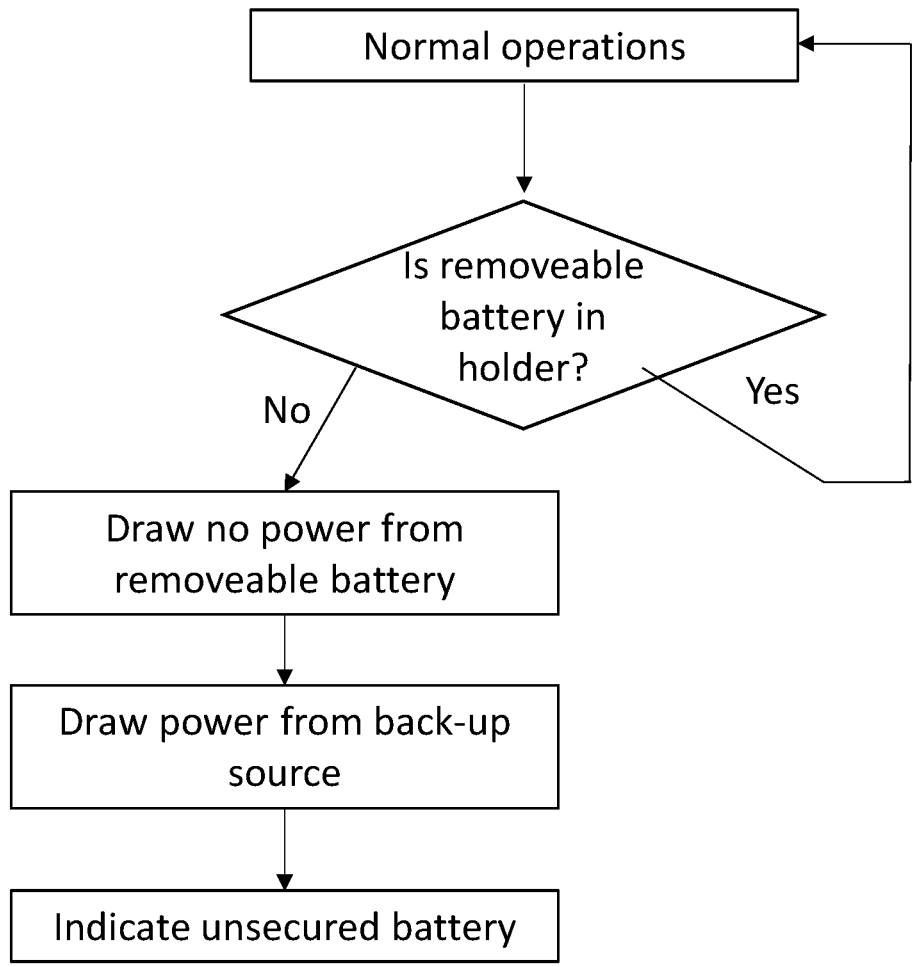
FIG. 8 is a flow chart with exemplary logic for operating the cart of FIGS. 5-6D.

FIG. 7 and FIG. 8 illustrates exemplary logic for operating the cart 110. The presence or non-presence of the removeable battery 120 within the holder 122 may be determined by the switch 113. The power bus 140 may begin and/or continue drawing power from the battery 120, as needed, upon the determination of presence of the battery 120. The power bus 140 may cease and/or not initiate drawings power from the battery 120 upon determination of non-presence of the battery 120. The power bus 140 may begin and/or continue drawing power from the back-up power source 138, as needed, upon the determination of non-presence of the battery 120. The power bus 140 may cease and/or not initiate drawings power from the back-up power source 138 upon determination of presence of the battery 120.

The current power sourcing status, such as whether the cart 110 is drawing power from one or both of the battery 120 and/or back-up power source 138, may be indicated at the cart 110. Such indication may be made by audible signal, visual signal, display at the display 42, some combination thereof, or the like. The amount of power being drawn from each source may be indicated along with other information such as, but not limited to, estimated power time remaining, capacity, voltage, current, run time, charging/discharging status, cycle count, some combination thereof, or the like.

Operations described herein may be performed, at least in part, by instruction from the controller 154.

Figure 9:
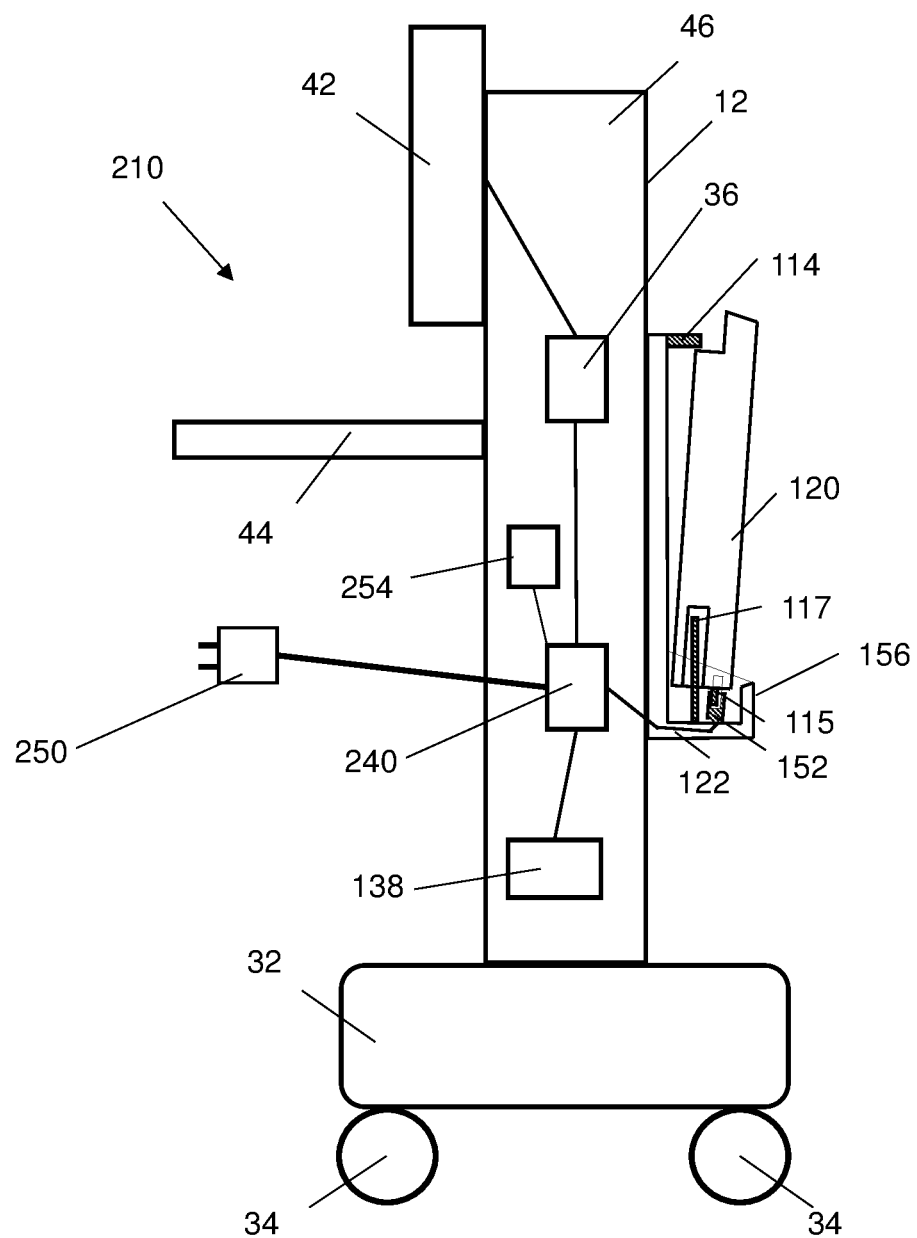
FIG. 9 is a side view of another exemplary cart with an exemplary automatic power sourcing system.

FIG. 9 illustrates another exemplary embodiment of the cart 210. A plug 250 may be provided for connection to wall outlet or other utility power. The plug 250 may be in electrical connection with a power bus 240. Operations described herein may be performed, at least in part, by instruction from the controller 254. The controller 254 may be configured to control certain operations of the cart 110 shown and described herein.

Figure 10:
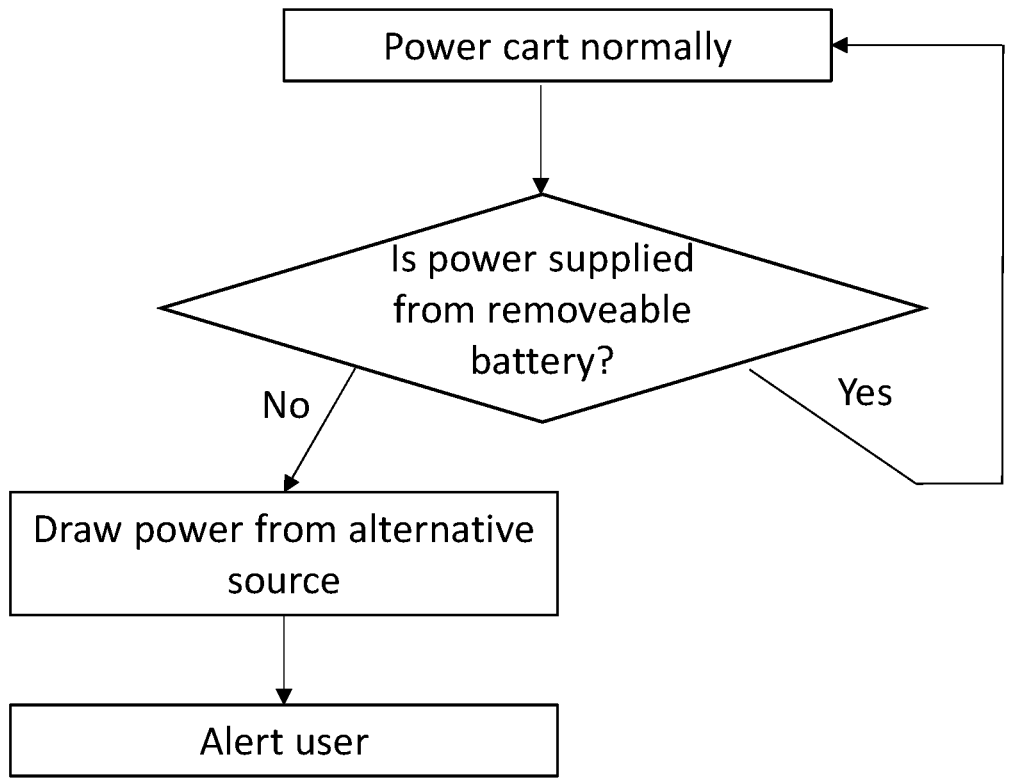
FIG. 10 is a flow chart with other exemplary logic for operating the cart of FIG. 9.

FIG. 10 illustrates exemplary logic for operating the cart 210. The cart 210 may be operated normally. Such normal operation may comprise drawing power from the removeable battery 120, utility power (via the plug 250), and/or the backup battery 138. Normal operations may continue until an unexpected loss of power event is determined such as, but not limited to, removal, dislodgement, disconnection, or the like of the battery 120. Upon determination of the unexpected loss of power event, the power bus 240 may be configured to automatically begin drawing power from an alternative power source, such as but not limited to, the back-up battery 138, utility power (via the plug 250), some combination thereof, or the like. Drawing of power from the alternative power source may occur automatically and may occur only after determination of the unexpected loss of power event. In exemplary embodiments, the unexpected loss of power event may be determined by a voltage drop, spike, current drop, spike, capacity loss, some combination thereof, or the like. The user may be alerted to the unexpected loss of power event by audible signal, visual signal, display at the display 42, some combination thereof, or the like. Operations described herein may be performed, at least in part, by instruction from the controller 254.

Figure 11:
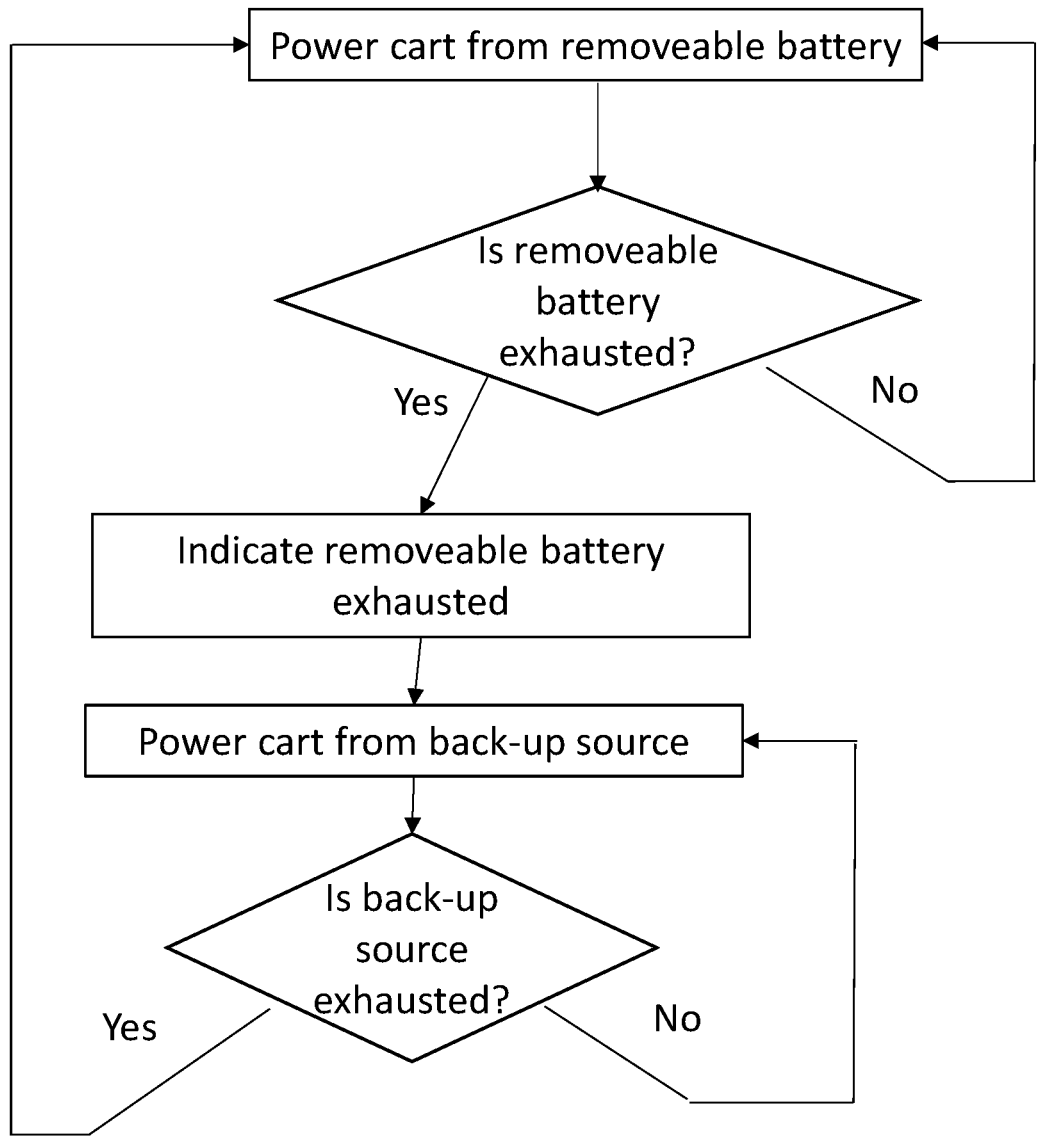
FIG. 11 is a flow chart with other exemplary logic for operating the cart of FIG. 9.

FIG. 11 illustrates other exemplary logic for operating the cart 210. The cart 210 may be configured to draw power from the removeable battery 120 until capacity of the removeable battery 120 is exhausted. After exhaustion of the removeable battery 120, the power bus 240 may automatically draw power from an alternative power source, such as but not limited to, the back-up battery 138, utility power supply (via the plug 250), some combination thereof, or the like. Drawing of power from the alternative power source may occur automatically and may occur only after exhaustion of the battery 120 is completed. In exemplary embodiments, the loss of capacity may be determined by a voltage drop, spike, current drop, spike, capacity loss, some combination thereof, or the like.

The power bus 240 may automatically power the cart 210 from the alternative power source until the alternative power source is exhausted. Following such exhaustion of the alternative power source, the power bus 240 may draw power from the removeable battery 120. Alternatively, or additionally, the power bus 240 may automatically power the cart 210 from the alternative power source until capacity of the removeable battery 120 is restored, such as but not limited to a non-zero capacity, or capacity above the threshold.

The user may be alerted to the loss of capacity and/or change in power sourcing by audible signal, visual signal, display at the display 42, some combination thereof, or the like. The user may alternatively, or additionally, be provided one or more warning alerts indicating capacity below a certain threshold (e.g., 10%).

The drawing of power from a particular power source (e.g., battery 120, back-up batter 138, plug 250) as described herein may be realized exclusively or in combination with drawing power from other power sources (e.g., battery 120, back-up batter 138, plug 250).

Operations described herein may be performed, at least in part, by instruction from the controller 254.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may be personal computers, smartphones, tablets, databases, servers, or the like. The electronic connections described herein may be accomplished by wired or wireless means.

What is claimed is:

1. A mobile medical cart providing data continuity, said mobile medical cart comprising:
   a base comprising one or more wheels;
   a body extending from said base;
   a holder mounted to the body and configured to receive a removable battery comprising a terminal and defining a cavity;
   a connector located at the holder at a position to receive the terminal when said removable battery is positioned within the holder;
   an alternative power source;
   a power bus in electrical connection with the connector and the alternative power source;
   an obstruction configured to physically obstruct removal of the removable battery from the holder while said removable battery is located in a secured position within said holder until said removable battery is moved to an unsecured position within said holder;
   a protrusion located at said holder, wherein said cavity is configured to accept said protrusion when said removable battery is placed within said holder in the secured position or the unsecured position, wherein said protrusion is configured to align said terminal with said connector;

a detector positioned and configured to detect movement of said removable battery into said unsecured position; and a controller in electrical connection with the power bus and the detector, wherein said controller is configured to command said power bus to automatically cease sourcing power from said removable battery and begin sourcing power from the alternative power source following receipt of one or more signals from said detector indicating that the removable battery is no longer in said secured position;

wherein said connector is configured for movement sufficient to maintain an electrical connection between said terminal and said connector while said removable battery is positioned within said holder and moved between said secured position and said unsecured position.

2. The mobile medical cart of claim 1 further comprising:
an electronic display mounted to said body, wherein the controller is configured to generate an alert regarding movement of said removable battery from said secured position for display at said electronic display.

3. The mobile medical cart of claim 1 wherein:
the alternative power source comprises a back-up battery permanently or semi-permanently installed at said body.

4. The mobile medical cart of claim 3 wherein:
the alternative power source comprises utility power provided by a plug for a wall outlet.

5. The mobile medical cart of claim 1 wherein:
said holder is configured to receive said removable battery in a vertical orientation.

6. The mobile medical cart of claim 1 wherein:
said detector comprises a switch located on a surface of said holder; and
said switch is positioned for activation when said removable battery is placed in said secured position within said holder.

7. The mobile medical cart of claim 1 wherein:
said controller is configured to automatically cease sourcing power from said alternative power source and begin sourcing power from the removable battery following receipt of one or more signals from said detector indicating that said one of said removable battery is in said secured position.

8. A mobile medical cart providing data continuity, said mobile medical cart comprising:
a base comprising one or more wheels;
a body extending from said base;
a holder mounted to said body in a moveable manner to permit movement between a first position where an upper end of said holder is located against said body and a second position where said upper end of said holder is moved away from said body, wherein said holder is configured to removably receive a battery;
a connector associated with the holder and configured to electrically connect with one or more terminals of said battery when said battery is positioned within the holder and said holder is moved between said first and second positions;
an alternative power source;
a power bus in electrical connection with the connector and the alternative power source;
an obstruction configured to physically obstruct removal of the battery from the holder while said holder is in the first position but not when the holder is moved to the second position;
a detector positioned between said body and said holder so as to be activated when said holder is moved between said first and second positions; and
a controller in electrical connection with the power bus and the detector, wherein said controller is configured to command said power bus to automatically cease sourcing power from said battery and begin sourcing power from the alternative power source following a receipt of one or more signals from said detector indicating that the holder is no longer in the first position.

9. The mobile medical cart of claim 8 wherein:
said detector comprises a switch.

10. The mobile medical cart of claim 9 wherein:
said terminal is located on a bottom surface of said holder.

11. A mobile medical cart providing data continuity, said mobile medical cart comprising:
a body;
a holder associated with the body and configured to removably receive a battery;
a connector which provides electrical connection with said battery when said battery is placed in a secured position within the holder where said battery and said holder are positioned proximate to said body and an unsecured position where at least a portion of said battery is moved away from said body;
an alternative power source;
a power bus electrically connected with the connector and the alternative power source;
an obstruction which physically prevents removal of said battery from said holder while said battery is in the secured position and permits removal of the battery from said holder when the battery is placed the unsecured position;
a detector which senses movement of said battery into said unsecured position; and
a controller in electrical connection with the power bus and the detector and configured to command said power bus to automatically cease sourcing power from said battery and begin sourcing power from the alternative power source following a receipt of one or more signals from said detector indicating that the battery is no longer in said secured position.

12. The system of claim 11 further comprising:
a base comprising one or more wheels; and
a body which extends from the base, wherein said holder is associated with said body.

13. The system of claim 12 wherein:
said holder is fixed or moveable relative to said body.

14. The system of claim 13 wherein:
said obstruction comprises a fixed, rigid structure which protrudes from a centerline of said body.

* * * * *